US008877764B2

(12) United States Patent
Solca

(10) Patent No.: US 8,877,764 B2
(45) Date of Patent: *Nov. 4, 2014

(54) METHOD FOR TREATING CANCER HARBORING EGFR MUTATIONS

(75) Inventor: Flavio Solca, Vienna (AT)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 420 days.

This patent is subject to a terminal disclaimer.

(21) Appl. No.: 12/441,180

(22) PCT Filed: Sep. 14, 2007

(86) PCT No.: PCT/EP2007/059735
§ 371 (c)(1),
(2), (4) Date: Apr. 9, 2009

(87) PCT Pub. No.: WO2008/034776
PCT Pub. Date: Mar. 27, 2008

(65) Prior Publication Data
US 2009/0318480 A1    Dec. 24, 2009

(30) Foreign Application Priority Data

Sep. 18, 2006  (EP) ..................................... 06120856
Jan. 31, 2007  (EP) ..................................... 07101505

(51) Int. Cl.
*A61K 31/517*    (2006.01)
(52) U.S. Cl.
CPC .................... *A61K 31/517* (2013.01)
USPC .................................................. 514/266.24
(58) Field of Classification Search
USPC .................................................. 514/266.24
See application file for complete search history.

(56) References Cited

U.S. PATENT DOCUMENTS

| | | | |
|---|---|---|---|
| 5,728,687 A | 3/1998 | Bissery | |
| 5,866,572 A | 2/1999 | Barker et al. | |
| 6,127,374 A | 10/2000 | Bridges | |
| 6,153,617 A | 11/2000 | Bridges | |
| 6,251,912 B1 | 6/2001 | Wissner et al. | |
| 6,297,258 B1 | 10/2001 | Wissner et al. | |
| 6,344,459 B1 | 2/2002 | Bridges et al. | |
| 6,362,336 B1 | 3/2002 | Lohmann et al. | |
| 6,403,580 B1 | 6/2002 | Himmelsbach et al. | |
| 6,617,329 B2 | 9/2003 | Himmelsbach et al. | |
| 6,627,634 B2 | 9/2003 | Himmelsbach et al. | |
| 6,653,305 B2 | 11/2003 | Himmelsbach et al. | |
| 6,656,946 B2 | 12/2003 | Himmelsbach et al. | |
| 6,673,803 B2 | 1/2004 | Thomas et al. | |
| 6,740,651 B2 | 5/2004 | Himmelsbach et al. | |
| 6,924,285 B2 | 8/2005 | Himmelsbach et al. | |
| 6,972,288 B1 | 12/2005 | Himmelsbach et al. | |
| 7,019,012 B2 | 3/2006 | Himmelsbach et al. | |
| 7,084,136 B2 | 8/2006 | Tanimoto et al. | |
| 7,119,084 B2 | 10/2006 | Himmelsbach et al. | |
| 7,160,889 B2 | 1/2007 | Hennequin et al. | |
| 7,196,091 B2 | 3/2007 | Himmelsbach et al. | |
| 7,220,750 B2 | 5/2007 | Himmelsbach et al. | |
| 7,223,749 B2 | 5/2007 | Himmelsbach et al. | |
| 7,456,189 B2 | 11/2008 | Himmelsbach et al. | |
| 7,846,936 B2 | 12/2010 | Hilberg et al. | |
| 7,960,546 B2 | 6/2011 | Schroeder et al. | |
| 8,067,593 B2 | 11/2011 | Schroeder et al. | |
| RE43,431 E | 5/2012 | Himmelsbach et al. | |
| 8,188,274 B2 | 5/2012 | Schroeder et al. | |
| 8,404,697 B2 | 3/2013 | Solca et al. | |
| 2001/0044435 A1 | 11/2001 | Himmelsbach et al. | |
| 2002/0032208 A1 | 3/2002 | Lohmann et al. | |
| 2002/0077330 A1 | 6/2002 | Himmelsbach et al. | |
| 2002/0082270 A1 | 6/2002 | Himmelsbach et al. | |
| 2002/0169180 A1 | 11/2002 | Himmelsbach et al. | |
| 2002/0173509 A1 | 11/2002 | Himmelsbach et al. | |

(Continued)

FOREIGN PATENT DOCUMENTS

DE    19825591 A1    12/1999
DE    19908567 A1    8/2000

(Continued)

OTHER PUBLICATIONS

Calabresi P and Chabner BA, "Section IX Chemotherapy of Neoplastic Diseases—Introduction," Goodman & Gilman's The Pharmacological Basis of Therapeutics 10th ed., 2001, Hardman JG, Limbird LE, and Gilman AG, Eds, McGraw-Hill, New York 2001, 1381-1388 (pp. 1381, 1383-1385, and 1388 provided).*
Stedman's Medical Dictionary, 27th ed., Lippincott, Eilliams & Wilkins, Baltimore, 2000.*
Chan SK, Gullick WJ, Hill ME. Mutations of the epidermal growth factor receptor in non-small cell lung cancer—search and destroy. Eur J Cancer. Jan. 2006;42(1):17-23.*
Solca et al.; 567 POSTER Efficacy of BIBW 2992, an irreversible dual EGFR/HER2 receptor tyrosine kinase inhibitor, in combination with cytotoxic agents; European Journal of Cancer; Supplement; Nov. 2006; vol. 4; No. 12; Pergamon; Oxford, GB.
Plummer et al.; 573 POSTER Phase I study of BIBW2992, an oral irreversible dual EGFR/HER2 inhibitor, showing activity in tumors with mutated EGFR; European Journal of Cancer; Supplement; Nov. 2006; vol. 4; No. 12; Pergamon; Oxford, GB.

(Continued)

*Primary Examiner* — Paul Zarek
(74) *Attorney, Agent, or Firm* — Michael P. Morris; Anthony P. Bottino

(57) ABSTRACT

The present invention relates to a method of treatment of patients suffering from cancer and harboring mutations of EGFR in the tumor, for instance an activating mutation of the EGFR or a mutation responsible for resistance or the emergence of acquired resistance to treatment with reversible EGFR and/or HER2 inhibitors or irreversible inhibitors such as CI-1033, EKB-569, HKI-272 or HKI-357, comprising administering an effective amount of the irreversible EGFR inhibitor BIBW2992 (1) 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline, to a person in need of such treatment, optionally in combination with the administration of a further chemotherapeutic agent, in combination with radiotherapy, radio-immunotherapy and/or tumor resection by surgery, and to the use of a BIBW 2992 (1) for preparing a pharmaceutical composition for the treatment of patients suffering from cancer and harboring mutations of EGFR in the tumor.

5 Claims, No Drawings

(56) References Cited

U.S. PATENT DOCUMENTS

| | | |
|---|---|---|
| 2003/0149062 A1 | 8/2003 | Jung et al. |
| 2003/0191308 A1 | 10/2003 | Hennequin et al. |
| 2003/0225079 A1 | 12/2003 | Singer et al. |
| 2004/0024019 A1 | 2/2004 | Tanimoto et al. |
| 2004/0158065 A1 | 8/2004 | Barth et al. |
| 2005/0043233 A1 | 2/2005 | Stefanic et al. |
| 2005/0085495 A1 | 4/2005 | Soyka et al. |
| 2005/0215574 A1 | 9/2005 | Bradbury et al. |
| 2006/0058311 A1 | 3/2006 | Munzert et al. |
| 2006/0100223 A1 | 5/2006 | Himmelsbach et al. |
| 2006/0270672 A1 | 11/2006 | Himmelsbach et al. |
| 2007/0027170 A1 | 2/2007 | Soyka et al. |
| 2007/0078091 A1 | 4/2007 | Hubler et al. |
| 2007/0099918 A1 | 5/2007 | Singer et al. |
| 2007/0185091 A1 | 8/2007 | Himmelsbach et al. |
| 2008/0096212 A1 | 4/2008 | Bell et al. |
| 2008/0103161 A1 | 5/2008 | Himmelsbach et al. |
| 2008/0207615 A1 | 8/2008 | Bell et al. |
| 2008/0234264 A1 | 9/2008 | Bell et al. |
| 2008/0254040 A1 | 10/2008 | Stefanic et al. |
| 2008/0269487 A1 | 10/2008 | Bradbury et al. |
| 2009/0036676 A1 | 2/2009 | Himmelsbach et al. |
| 2009/0203683 A1 | 8/2009 | Himmelsbach et al. |
| 2009/0238828 A1 | 9/2009 | Munzert et al. |
| 2009/0306044 A1 | 12/2009 | Solca et al. |
| 2009/0306072 A1 | 12/2009 | Jung et al. |
| 2009/0306101 A1 | 12/2009 | Solca et al. |
| 2009/0306378 A1 | 12/2009 | Schroeder et al. |
| 2009/0318480 A1 | 12/2009 | Solca |
| 2010/0010023 A1 | 1/2010 | Himmelsbach et al. |
| 2010/0069414 A1 | 3/2010 | Himmelsbach et al. |
| 2010/0087482 A1 | 4/2010 | Haber et al. |
| 2010/0144639 A1 | 6/2010 | Singer et al. |
| 2011/0039863 A1 | 2/2011 | Hilberg et al. |
| 2011/0046168 A1 | 2/2011 | Himmelsbach et al. |
| 2011/0142929 A1 | 6/2011 | Messerschmid et al. |
| 2011/0171289 A1 | 7/2011 | Stefanic et al. |
| 2011/0207929 A1 | 8/2011 | Schroeder et al. |
| 2011/0207932 A1 | 8/2011 | Schroeder et al. |
| 2012/0107399 A1 | 5/2012 | Barta |
| 2012/0157472 A1 | 6/2012 | Larsen et al. |
| 2012/0329778 A1 | 12/2012 | Himmelsbach et al. |
| 2013/0012465 A1 | 1/2013 | Haslinger et al. |

FOREIGN PATENT DOCUMENTS

| | | |
|---|---|---|
| DE | 19911366 A1 | 9/2000 |
| DE | 10017539 A1 | 10/2001 |
| DE | 10042060 A1 | 3/2002 |
| DE | 10042064 A1 | 3/2002 |
| EP | 0302967 A2 | 2/1989 |
| EP | 0566226 A1 | 10/1993 |
| EP | 0799619 A2 | 10/1997 |
| EP | 1123705 A1 | 8/2001 |
| WO | 9410995 A1 | 5/1994 |
| WO | 9520045 A1 | 7/1995 |
| WO | 9630347 A1 | 10/1996 |
| WO | 9633980 A1 | 10/1996 |
| WO | 9702266 A1 | 1/1997 |
| WO | 9738983 A1 | 10/1997 |
| WO | 9843960 A1 | 10/1998 |
| WO | 9906378 A1 | 2/1999 |
| WO | 9906396 A1 | 2/1999 |
| WO | 9909016 A1 | 2/1999 |
| WO | 9933980 A2 | 7/1999 |
| WO | 9935146 A1 | 7/1999 |
| WO | 9965228 A2 | 12/1999 |
| WO | 0018740 A1 | 4/2000 |
| WO | 0031048 A1 | 6/2000 |
| WO | 0031068 A1 | 6/2000 |
| WO | 0051991 A1 | 9/2000 |
| WO | 0055141 A1 | 9/2000 |
| WO | 0078735 A1 | 12/2000 |
| WO | 0134574 A1 | 5/2001 |
| WO | 0168186 A2 | 9/2001 |
| WO | 0177104 A1 | 10/2001 |
| WO | 0218351 A1 | 3/2002 |
| WO | 0218372 A1 | 3/2002 |
| WO | 0218373 A1 | 3/2002 |
| WO | 0218375 A1 | 3/2002 |
| WO | 0218376 A1 | 3/2002 |
| WO | 0241882 A2 | 5/2002 |
| WO | 0250043 A1 | 6/2002 |
| WO | 03082290 A1 | 10/2003 |
| WO | 03089439 A1 | 10/2003 |
| WO | 03094921 A2 | 11/2003 |
| WO | 2004014426 A1 | 2/2004 |
| WO | 2004074263 A1 | 9/2004 |
| WO | 2004096224 A2 | 11/2004 |
| WO | 2004108664 A2 | 12/2004 |
| WO | 2005033096 A1 | 4/2005 |
| WO | 2005037824 A2 | 4/2005 |
| WO | 2006017317 A2 | 2/2006 |
| WO | 2006018182 A1 | 2/2006 |
| WO | 2006084058 A2 | 8/2006 |
| WO | 2007054550 A1 | 5/2007 |
| WO | 2007054551 A1 | 5/2007 |
| WO | 2007085638 A1 | 8/2007 |
| WO | 2008034776 A1 | 3/2008 |
| WO | 2009147238 A1 | 12/2009 |
| WO | 2010081817 A1 | 7/2010 |
| WO | 2011003853 A2 | 1/2011 |
| WO | 2011069962 A1 | 6/2011 |

OTHER PUBLICATIONS

International Search Report, Form PCT/ISA210, for corresponding PCT/EP2007/059735, date of mailing: Dec. 6, 2007.

U.S. Appl. No. 12/093,322, filed May 10, 2008; Solca et al.; Combination Treatment of Cancer Comprising EGFR/HER2 Inhibitors.

Agus, D.B. et al., Abstract: "A phase I dose escalation study of BIBW 2992, an irreversible dual EGFR/HER2 receptor tyrosine kinase inhibitor, in a continuous schedule in patients with advanced solid tumours." Journal of Clinical Oncology, 2006, ASCO Annual Meeting Proceedings (Post-Meeting Edition). vol. 24, No. 18S, (Jun. 20 Supplement), 2006, 2074.

Lewis, N., et al. Abstract: "A phase I dose escalation study of BIBW 2992, an irreversible dual EGFR/HER2 receptor tyrosine kinase inhibitor, in a 3 week on 1 week off schedule in patients with advanced solid tumors". Journal of Clinical Oncology, 2006 ASCO Annual Meeting Proceedings (Post-Meeting Edition). vol. 24, No. 18S (Jun. 20 Supplement), 2006: 3091.

International Search Report and Written Opinion for PCT/EP2007/059735 date mailed Dec. 6, 2007.

Sequist, L.V., et al., "Neratinib, an Irrerversible Pan-ErbB Receptor Tyrosine Kinase Inhibitor: Results of a Phase II Trial in Patients with Advanced Non-Small-Cell Lung Cancer" Journal of Clinical Oncology, vol. 28, No. 18, Jun. 20, 2010, p. 3076-3083.

Subramaniam, D. S., et al., "BIBW 2992 in non-small cell lung cancer". Expert Opinion, Drug Evaluation, 2011, vol. 20, No. 3, p. 415-422.

Abstract in English (2000) for DE19911366.

Abstract in English for WO199965228, 2010.

Alan, R. "Benign Prostatic Hyperplasia (BPH)". Available at http://healthlibrary.epnet.com/GetContent/asp?token-1baaea3c-d4f5-4e14-8429-e3b3e1add7a7&chunkiid-1203, last reviewed Mar. 2006.

Barton, J. et al., "Growth Factors and their Receptors: new Targets for Prostate Cancern Therapy". Urology 58 (Supplement 2A), Aug. 2001, p. 114-122.

Bell, D.W. et al., "Inherited susceptibility to lung cancer may be associated with the T790M drug resistance mutation in EGFR". Nature Genetics, Dec. 2005, vol. 37, No. 12, p. 1315-1316. Published online Oct. 30, 2005.

Boehringer Ingelheim Press Release "Resistance to Epidermal Growth Factor Receptor (EGFR) Tyrosine Kinase Inhibitors (TKIs)." 2010.

Boehringer Ingelheim, "BIBW 2992: A Potent and Irreversible Inhibitor of EGFR/HER1 and HER2." Accessed on Jan. 3, 2012.

Boschelli, D., "4-Anilino-3-quinolinecarbonitriles: An Emerging Class of Kinase Inhibitors—An Update." Medicinal Chemistry Reviews—Online, 2004, vol. 1, pp. 457-463.

(56) References Cited

OTHER PUBLICATIONS

Burris, HA et al.; "EGF1004: a randomized, multicenter, phase 1b study of the safety, biologic activity and clinical efficacy of the dual kinase inhibitor GW572016" Breast Cancer Research and Treatment, V. 82, suppl. 1 (2003), p. S18 #39.

Camp, E. et al., "Molecular Mechanisms of Resistance to Therapies Targeting the Epidermal Growth Factor Receptor." Clinical Cancer Research, 2005, vol. 11, No. 1, pp. 397-405.

Cancer Genome and Collaborative Group. Nature, Brief Communications, Sep. 2004, vol. 431, p. 525-526.

Choong, N. et al., "Gefitinib Response of Erlotinib-refractory Lung Cancer Involving Meninges—Role of EGFR Mutation." Nature Clinical Practice Oncology, 2006, vol. 3, No. 1, pp. 50-57.

deMiguel, M. et al., "Immunohistochemical comparative analysis of transforming grwoth factor a, epidermal growth factor, and epidermal growth factor receptor in normal, hyperplastic and neoplastic human prostates". Cytokine, 1998, p. 722-727.

Drug Data Report, "BIBW-2992" 2005, vol. 27, No. 11.

Duque, J.L. et al., "Heparin-Binding Epidermal Growth Factor-Like Growth Factor is an Autocrine Mediator of Human Prostate Stromal Cell Growth in Vitro". The Journal of Urology, vol. 165, Jan. 2001, p. 284-288.

Gonzales-Barcena, D. et al., "Responses to the antagonistic analog of LH-RH (SB-75, cetrorelix) in patients with benign prostatic hyperplasia and prostatic cancer". The Prostate, 1994, 24(2), p. 84-92, only abstract provided.

Harari, P.M. "Epidermal growth factor receptor inhibition strategies in oncology". Endocrine-Related Cancer, 2004, vol. 11. p. 689-708.

Herbst, R.S. et al., "Monoclonal Antibodies to Target Epidermal Growth Factor Receptor-Positive Tumors". Cancer, Mar. 1, 2002, vol. 94, No. 5, p. 1593-1611.

Hirsh, V., "Afatinib (BIBW 2992) Development in Non-Small-Cell Lung Cancer." Future Oncology, 2011, vol. 7, pp. 817-825.

Hofmann, B .B., Chapter 10 Catecholamines, Sympathomimetic Drugs, and Adrenergic Receptor Antagonists. "Goodman and Gilman's the Pharmacological Basis of Therapeutics, 10th ed." Hardman JG, Limbird, LE, and Gilman AG, Eds. McGraw-Hill, 2001, p. 215-268, pp. 215, 247 and 248 provided).

International Search Report for PCT/EP01/14569 mailed Mar. 1, 2002.

Johnson, J, et al. "Relationships between drug activity in NCI preclinical in vitro and in vitro and in vivo models and early clinical trials". British Journal of Cancer, 2001, 84 (10, p. 1424-1431.

Kobayashi, S. et al.,"EGFR Mutation and Resistance of Non-Small-Cell Lung Cancer to Gefitinib." The New England Journal of Medicine, 2005, vol. 352, pp. 786-792.

Krozely, P. Abstract—Clinical Journal of Oncology Nursing, 2004, vol. 8, No. 2, p. 1092-1095.

Kwak, E. et al. "Irreversible Inhibitors of the EGF Receptor may Circumvent Acquired Resistance to Gefitinib." PNAS, 2005, vol. 102, No. 21, pp. 7665-7670.

Laird & Cherrington, "Small molecule tyrosine kinase inhibitors: clinical development of anticancer agents" Expert Opinion. Investig. Drugs.; Ashley Publications (2003) 12(1) p. 51-64.

Lee, M., "Tamsulosin for the Treatment of Benigh Prostatic Hypertrophy". The Annals of Pharmacotherapy, Feb. 2000, 34, p. 188-199.

Li, D. et al. "BIBW2992, An Irreversible EGFR/HER2 Inhibitor Highly Effective in Preclinical Lung Cancer Models." Oncogene, 2008, vol. 27, No. 34, pp. 4702-4711.

McMahon; VEGF Receptor Signaling in Tumor Angiogenesis; The Oncologist; 2000; 5 (suppl 1); pp. 3-10.

Paez, J. G. "EGFR Mutations in Lung Cancer: Correlation with Clinical Response to Gefitinib Therapy". Science, vol. 304, 2004, p. 1497-1500.

Pinedo et al.; Translational Research: The Role of VEGF in Tumor Angiogenesis; The Oncologist; 2000; 5(suppl 1); pp. 1-2.

Rayford, W. et al., "Muscarinic Cholinergic Receptors Promote Growth of Human Prostate Cancer Cells". The Prostate, Feb. 1997, 30(3), p. 160-165.

Rosell, R. et al., "Crossing the Rubicon in Lung Adenocarcinoma: the Conundrum of EGFR Tyrosine Kinase Mutations." 2005, vol. 1, No. 3, pp. 319-322.

Sausville, E. A. et al. "Contributions of Human Tumor Xenografts to Anticancer Drug Development". Cancer Research, 2006, vol. 66 (7), p. 3351-3354.

Supplement ASCO Meeting Abstracts 1-4, Journal of Clinical Oncology, 2006.

Toyooka, S. et al., "EGFR Mutation and Response of Lung Cancer to Gefitinib." The New England Journal of Medicine, 2005, vol. 352, No. 20, p. 2136.

Tsou, Hwei-Ru, "6-Substituted-4-(3-bromophenylamino)quinazolines as Putative Irreversible Inhibitors of the Epidermal Growth Factor Receptor (EGFR) and Human Epidermal Growth Facotr Receptor (HER-2) Tyrosine Kinases with Enhanced Antitumore Activity", J. Med. Chem 2001, 2719-2734, vol. 44.

U.S. Appl. No. 12/914,003, filed Oct. 28, 2010, Inventor: Frank Himmelsbach.

Wikstrand, C. et al. "Monoclonal Antibodies against EGFRvIII Are Tumor Specific and React with Breast and Lung Carcinomas and Malignant Gliomas." Cancer Research, 1995, vol. 55, No. 14, pp. 3140-3148.

Wissner, A. et al., "Synthesis and Structure—Activity Relationships of 6,7-Disubstituted 4-Anilinoquinoline-3-carbonitriles. The Design of an Orally Active, Irreversible Inhibitor of the Tyrosine Kinase Activity of the Epidermal Growth Factor Receptor (EGFR) and the Human Epidermal Growth Factor Receptor-2 (HER-2)." Journal of Medicinal Chemistry, 2003, vol. 46, pp. 49-63.

Xu, Y. et al., "Acquired Resistance of Lung Adenocarcinoma to EGFR-tyrosine Kinase Inhibitors Gefitinib and Erlotinib." Cancer Biology & Therapy, 2010, vol. 9, No. 8, pp. 572-582.

Yanase, K. et al., "Gefitinib reverses breast cancer resistance protein-medicated drug resistance". Molecular Cancer Therapeutics, 2004, Vo. 9, No. 9, p. 119-1125.

Fry, David W., "Inhibition of the Epidermal Growth Factor Receptor Family of Tyrosine Kinases as an Approach to Cancer Chemotherapy Progression from Reversible to Irreversible Inhibitors." Pharmacological & Therapeutics, 1999, vol. 82, No. 2-3, pp. 207-218.

Goodman & Gilman's, "The Pharmacological Basis of Therapeutics" Tenth Edition, 2001, pp. 1381-1388.

Solca, F. et al., "A242 BIBW 2992, an Irreversible Dual EGFR/HER2 Kinase Inhibitor, Shows Activity on L858R/T790M EGFR Mutants." and "A244 BIBW 2992, An Irreversible Dual EGFR/HER2 Receptor Tyrosine Kinase Inhibitor for Cancer Therapy." Molecular Targets and Cancer Therapeutics, Nov. 2005.

Yoshimura, N. et al., "EKB-569, a new irreversible epidermal growth factor recptor tyrosine kinase inhibitor, with clinical activity in patients with non-small cell lung cancer with acquired resistance to gefitinib." Lung Cancer, 2006, vol. 51, pp. 363-368.

* cited by examiner

METHOD FOR TREATING CANCER HARBORING EGFR MUTATIONS

RELATED APPLICATIONS

This application is a Section 371 (35 U.S.C.) filing of International Application No. PCT/EP2007/059735, which International Application was filed Sep. 14, 2007, and claims priority to European Patent Application No. 06120856.7, filed Sep. 18, 2006, and European Patent Application No. 07101505.1, filed Jan. 31, 2007, the contents of all of which are incorporated herein by reference in their entirety.

The present invention relates to a method of treating patients suffering from cancer and harbouring mutations of EGFR in the tumour. The said method comprises administration of an effective amount of the irreversible EGFR inhibitor BIBW2992 (1) to a person in need of such treatment, optionally in combination with the administration of a further chemotherapeutic agent (2), in combination with radiotherapy, radio-immunotherapy and/or tumour resection by surgery. The mutation of the EGFR encompasses at least all amplifications or activating gene mutations that are relevant to enhanced expression (e.g. reduced CA-repeats (CA: cytosine-adenosine) in the first intron or other specific polymorphisms), increased sensitivity to activation or genuinely activating mutations (e.g. L858R or G719S point mutations or specific exon 19 deletions). It also includes those mutations associated with resistance (e.g. D761Y, insertions D770_N771insNPG) or emergence of acquired resistance (e.g. T790M) to treatment with reversible EGFR and/or HER2 inhibitors such as gefitinib, erlotinib, vandetanib (ZD-6474), AEE-788, PKI-166, lapatinib, cetuximab, nimotuzumab, matuzumab, panitumumab, trastuzumab and pertuzumab or other irreversible inhibitors such asCI-1033, EKB-569, HKI-272 or HKI-357.

BACKGROUND OF THE INVENTION

Somatic mutations in the tyrosine kinase (TK) domain of the epidermal growth factor receptor (EGFR) gene in lung cancers have generated enormous interest, providing an approach to predict for sensitivity to TK inhibitors (TKIs). While mutational status is of great importance in determining response to TKIs, it is not the sole factor, and evidence is accumulating that EGFR gene amplification, other members of the EGFR family (HER2, HER3) and genes downstream of EGFR signaling (KRAS, BRAF), may be involved in cancer pathogenesis and the response of TKIs.

WO 2006/084058 discloses a method for the treatment of gefitinib and/or erlotinib resistant cancer comprising administered a pharmaceutical composition comprising an irreversible epidermal growth factor receptor (EGFR) inhibitor to a person in need of such treatment, specifying the irreversible EGFR inhibitors EKB-569, HKI-272 and HKI-357.

Epithelial cell cancers, for example, prostate cancer, breast cancer, colon cancer, lung cancer, pancreatic cancer, ovarian cancer, cancer of the spleen, testicular cancer, cancer of the thymus, etc., are diseases characterized by abnormal, accelerated growth of epithelial cells. This accelerated growth initially causes a tumor to form. Eventually, metastasis to different organ sites can also occur. Although progress has been made in the diagnosis and treatment of various cancers, these diseases still result in significant mortality.

Lung cancer remains the leading cause of cancer death in industrialized countries. Cancers that begin in the lungs are divided into two major types, non-small cell lung cancer and small cell lung cancer, depending on how the cells appear under a microscope. Non-small cell lung cancer (squamous cell carcinoma, adenocarcinoma, and large cell carcinoma) generally spreads to other organs more slowly than does small cell lung cancer. About 75 percent of lung cancer cases are categorized as non-small cell lung cancer (e.g., adenocarcinomas), and the other 25 percent are small cell lung cancer. Non-small cell lung cancer (NSCLC) is the leading cause of cancer deaths in the United States, Japan and Western Europe. For patients with advanced disease, chemotherapy provides a modest benefit in survival, but at the cost of significant toxicity, underscoring the need for therapeutic agents that are specifically targeted to the critical genetic lesions that direct tumor growth (Schiller J H et al., N Engl J Med, 346: 92-98, 2002).

Two of the more advanced compounds in clinical development include Gefitinib (compound ZD 1839 developed by AstraZeneca UK Ltd.; available under the tradename IRESSA; hereinafter "IRESSA") and Erlotinib (compound OSI-774 developed by Genentech, Inc. and OSI Pharmaceuticals, Inc.; available under the tradename TARCEVA; hereinafter "TARCEVA"); both have generated encouraging clinical results. Conventional cancer treatment with both IRESSA and TARCEVA involves the daily, oral administration of no more than 500 mg of the respective compounds. In May, 2003, IRESSA became the first of these products to reach the United States market, when it was approved for the treatment of advanced non-small cell lung cancer patients. IRESSA is an orally active quinazoline that functions by directly inhibiting tyrosine kinase phosphorylation on the EGFR molecule. It competes for the adenosine triphosphate (ATP) binding site, leading to suppression of the HER-kinase axis. The exact mechanism of the IRESSA response is not completely understood, however, studies suggest that the presence of EGFR is a necessary prerequisite for its action.

A significant limitation in using these compounds is that recipients thereof may develop a resistance to their therapeutic effects after they initially respond to therapy, or they may not respond to EGFR-tyrosine kinase inhibitots (TKIs) to any measurable degree at all. The response rate to EGFR-TKIs varies between different ethnic groups. At the low end of EGFR-TKI responders, in some populations, only 10-15 percent of advanced non-small cell lung cancer patients respond to EGFR kinase inhibitors. Thus, a better understanding of the molecular mechanisms underlying sensitivity to IRESSA and TARCEVA would be extremely beneficial in targeting therapy to those individuals whom are most likely to benefit from such therapy.

There is a significant need in the art for a satisfactory treatment of cancer, and specifically epithelial cell cancers such as lung, ovarian, breast, brain, colon and prostate cancers, which incorporates the benefits of TKI therapy and overcoming the non-responsiveness exhibited by patients. Such a treatment could have a dramatic impact on the health of individuals, and especially older individuals, among whom cancer is especially common.

BIBW2992 (1) is known as the compound 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline,

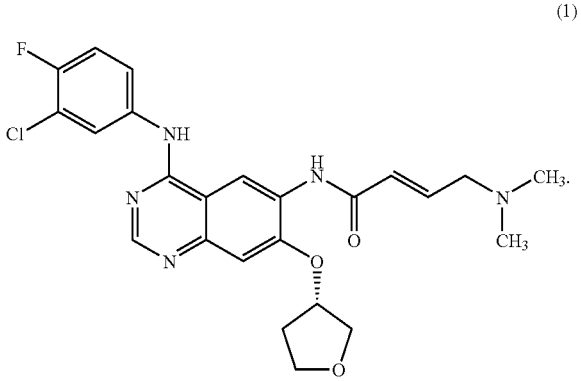 [SMILES: CN(C)C/C=C/C(=O)Nc1cc2c(Nc3ccc(F)c(Cl)c3)ncnc2cc1O[C@H]1CCOC1]

(1)

BIBW 2992 (1) is a potent and selective dual inhibitor of erbb1 receptor (EGFR) and erbB2 (Her2/neu) receptor tyrosine kinases. Furthermore, BIBW 2992 (1) was designed to covalently bind to EGFR and HER2 thereby irreversibly inactivating the receptor molecule it has bound to. This compound, salts thereof such as the dimaleate salt, their preparation as well as pharmaceutical formulations comprising BIBW2992 (1) or a salt thereof are disclosed in WO 02/50043 and WO 2005/037824. These documents are incorporated by reference regarding these aspects.

SUMMARY OF THE INVENTION

Surprisingly, the irreversible dual EGFR/HER2 inhibitor BIBW2992 (1) is advantageously effective in the treatment of cancer in patients harbouring a mutation of the EGFR in the tumour, such as an activating mutation of the EGFR, especially where the activating mutation is associated with another mutation responsible for resistance or the emergence of acquired resistance to treatment with reversible EGFR inhibitors such as e.g. gefitinib and/or erlotinib or other irreversible inhibitors such as CI-1033, EKB-569, HKI-272 or HKI-357. Therefore. patients who show a reduced response or are not or no longer responding to gefitinib and/or erlotinib therapies may benefit from a BIBW 2992 treatment.

Thus, as a first aspect and in the broadest embodiment the present invention relates to a method of treating patients suffering from cancer and harbouring a mutation of the EGFR gene in the tumour, compared to the native sequence of the EGFR. The said method comprises administering an effective amount of the irreversible EGFR inhibitor BIBW2992 (1) to a person in need of such treatment, optionally in combination with the administration of a further chemotherapeutic agent (2), and/or optionally in combination with radiotherapy, radio-immunotherapy and/or tumour resection by surgery.

A second aspect of the present invention is the use of BIBW 2992 (1) for preparing a pharmaceutical composition for the treatment of a patient suffering from cancer and harbouring a mutation of the EGFR gene in the tumour, compared to the native receptor, optionally in combination with a further chemotherapeutic agent (2).

In a first preferred embodiment of the present invention the mutation of the EGFR gene is an activating mutation.

In a second preferred embodiment of the present invention the mutation of the EGFR is an activating mutation associated with a resistance or acquired resistance mutation to treatment with reversible EGFR and HER2 inhibitors such as gefitinib, erlotinib, vandetanib (ZD-6474), AEE-788, PKI-166, lapatinib, cetuximab, nimotuzumab, matuzumab, panitumumab, trastuzumab and pertuzumab or other irreversible inhibitors such as CI-1033, EKB-569, HKI-272 or HKI-357.

Thus, in one embodiment, the present invention provides a method for the treatment of cancer resistant to treatment with reversible EGFR inhibitors, such as gefitinib and/or erlotinib resistant cancer. In this embodiment, progression of cancer in a subject is monitored at a time point after the subject has initiated gefitinib and/or erlotinib treatment or treatment with another reversible EGFR inhibitor. Progression of the cancer is indicative of cancer that is resistant to treatment with the reversible EGFR inhibitor.

The progression of cancer may be monitored by methods well known to those of skill in the art. For example, the progression may be monitored by way of visual inspection of the cancer, such as, by means of X-ray, CT scan or MRI. Alternatively, the progression may be monitored by way of tumor biomarker detection.

In one embodiment, the patient is monitored at various time points throughout the treatment of the cancer. For example, the progression of a cancer may be monitored by analyzing the progression of cancer at a second time point and comparing this analysis to an analysis at a first time point. The first time point may be before or after initiation of gefittinib and/or erlotinib treatment and the second time point is after the first. An increased growth of the cancer indicates progression of the cancer.

In one embodiment, the cancer is epithelial cell cancer. In one embodiment, the cancer is gastrointestinal cancer, prostate cancer, ovarian cancer, breast cancer, head and neck cancer, esophageal cancer, lung cancer, non-small cell lung cancer, cancer of the nervous system, kidney cancer, retina cancer, skin cancer, liver cancer, pancreatic cancer, genitalurinary cancer and bladder cancer.

In one embodiment, the size of the cancer is monitored at additional time points, and the additional time points are after the second time point.

In one embodiment, the later time point is at least 2 months after the preceding time point. In one embodiment, the later time point is at least 6 months after preceding time point. In one embodiment, the later time point is at least 10 months after preceding time point. In one embodiment, the later time point is at least one year after preceding time point.

In another embodiment, the present invention provides a method of treating cancer, comprising administering to a subject having a mutation in EGFR, namely, a substitution of a methionine for a threonine at position 790, known as the T790M in the art, a pharmaceutical composition comprising an effective amount of BIBW 2992 (1). The T790M mutation confers resistance to gefitinib and/or erlotinib treatment.

DETAILED DESCRIPTION OF THE INVENTION

The broadest embodiments of the present invention are not restricted with regard to the mutation of the EGFR, that is any difference in the sequence of the EGFR gene compared to the native sequence is to be understood as a mutation within the embodiments of the invention defined hereinbefore, e.g. the EGFR mutations selected from the group consisting of mutations listed in table 1. All EGFR mutations mentioned in table 1 are described in the state of the art.

TABLE 1

| No. | Position | Amino Acid | Type |
|---|---|---|---|
| 1 | 1 | M1__A566del | activating |
| 2 | 30 | V30_K209del | activating |
| 3 | 30 | V30_R297 > G | activating |
| 4 | 297 | R297 > [aa30-297] | activating |
| 5 | 545 | E545-G627del | activating |
| 6 | 660 | V660L | activating |
| 7 | 660 | V660L | activating |
| 8 | 689 | p.Val689Met | activating |
| 9 | 690 | E690-end | activating |
| 10 | 700 | N700D | activating |
| 11 | 709 | E709K | activating |
| 12 | 709 | E709Q | activating |
| 13 | 709 | E709A + L858R | activating |
| 14 | 709 | E709G + L858R | activating |
| 15 | 709 | E709K + L858R | activating |
| 16 | 718 | L718P | activating |
| 17 | 719 | G719A | activating |
| 18 | 719 | G719C | activating |
| 19 | 719 | G719S | activating |
| 20 | 719 | G719D | activating |
| 21 | 720 | S720F | activating |
| 22 | 720 | S720P | activating |
| 23 | 735 | G735S | activating |
| 24 | 746 | E746__A750 > QP | activating |
| 25 | 746 | E746__A750del | activating |
| 26 | 746 | E746__S752 > A | activating |
| 27 | 746 | E746__S752 > V | activating |
| 28 | 746 | E746__S752del | activating |
| 29 | 746 | E746__T751 > A | activating |
| 30 | 746 | E746__A750 > DP | activating |
| 31 | 746 | E746__A750 > IP | activating |
| 32 | 746 | E746__A750 > RP | activating |
| 33 | 746 | E746__P753 > LS | activating |
| 34 | 746 | E746__P753 > VS | activating |
| 35 | 746 | E746__S752 > A | activating |
| 36 | 746 | E746__S752 > D | activating |
| 37 | 746 | E746__S752 > I | activating |
| 38 | 746 | E746__S752 > T | activating |
| 39 | 746 | E746__S752 > V | activating |
| 40 | 746 | E746__T751 > A | activating |
| 41 | 746 | E746__T751 > I | activating |
| 42 | 746 | E746__T751 > IP | activating |
| 43 | 746 | E746__T751 > V | activating |
| 44 | 746 | E746__T751 > VA | activating |
| 45 | 746 | E746__T751 > VP | activating |
| 46 | 746 | E746__P753 > LS | activating |
| 47 | 746 | E746__P753 > VS | activating |
| 48 | 746 | E746__S752 > D | activating |
| 49 | 746 | E746__S752 > I | activating |
| 50 | 746 | E746__S752 > T | activating |
| 51 | 746 | E746__T751 > I | activating |
| 52 | 746 | E746__T751 > IP | activating |
| 53 | 746 | E746__T751 > V | activating |
| 54 | 746 | E746__T751 > VA | activating |
| 55 | 746 | E746__T751 > VP | activating |
| 56 | 746 | E746__T751del | activating |
| 57 | 747 | L747-K754 > SR | activating |
| 58 | 747 | L747__E749del | activating |
| 59 | 747 | p.Leu747_Glu749del; p.Ala750Pro | activating |
| 60 | 747 | L747__P753 > S | activating |
| 61 | 747 | L747__S752 > Q | activating |
| 62 | 747 | L747__S752del | activating |
| 63 | 747 | L747__T751 > P | activating |
| 64 | 747 | L747__T751 > S | activating |
| 65 | 747 | L747__T751del | activating |
| 66 | 747 | L747-K754 > ST | activating |
| 67 | 747 | K745__L747del | activating |
| 68 | 747 | L747__A750 > P | activating |
| 69 | 747 | L747__P753 > Q | activating |
| 70 | 747 | L747__R748 > FP | activating |
| 71 | 747 | L747__S752 > QH | activating |
| 72 | 747 | L747__T751 > Q | activating |
| 73 | 750 | A750P | activating |
| 74 | 752 | S752_I759del | activating |
| 75 | 765 | p.Val765Ala | activating |
| 76 | 766 | M766__A767insAI | activating |
| 77 | 767 | A767__S768insSVA | activating |
| 78 | 767 | A767__S768insTLA | activating |
| 79 | 768 | S768I | activating |
| 80 | 773 | H773R | activating |
| 81 | 776 | R776C | activating |
| 82 | 783 | T783A | activating |
| 83 | 796 | G796S | activating |
| 84 | 804 | E804G | activating |
| 85 | 826 | N826S | activating |
| 86 | 835 | H835L | activating |
| 87 | 838 | L838V | activating |
| 88 | 839 | A839T | activating |
| 89 | 858 | L858R | activating |
| 90 | 861 | L861Q | activating |
| 91 | 863 | G863D | activating |
| 92 | 761 | D761N | resistance |
| 93 | 770 | D770__N771insNPG | resistance |
| 94 | 770 | D770__N771insSVD | resistance |
| 95 | 770 | D770__P772 > ASVDNR | resistance |
| 96 | 790 | T790M | resistance |
| 96-a | 870 | H870R | resistance |
| 97 | 884 | E884K | resistance |
| 98 | 46 | D46N; G63R | |
| 99 | 108 | R108K | |
| 100 | 263 | T263P | |
| 101 | 289 | A289D | |
| 102 | 289 | A289T | |
| 103 | 289 | A289V | |
| 104 | 324 | R324L | |
| 105 | 330 | E330K | |
| 106 | 596 | P596L | |
| 107 | 598 | G598V | |
| 108 | 624 | C624F | |
| 109 | 624 | C624F | |
| 110 | 688 | L688P | |
| 111 | 694 | P694L | |
| 112 | 694 | P694S | |
| 113 | 703 | L703V | |
| 114 | 707 | L707L | |
| 115 | 715 | I715S | |
| 116 | 718 | L718L | |
| 117 | 719 | G719C + S768I | |
| 118 | 719 | G719S + S768I | |
| 119 | 724 | G724S | |
| 120 | 725 | T725M | |
| 121 | 727 | Y727C | |
| 122 | 729 | G729E | |
| 123 | 730 | L730F | |
| 124 | 731 | W731* | |
| 125 | 733 | P733L | |
| 126 | 734 | E734K | |
| 127 | 735 | G735S | |
| 128 | 742 | V742A | |
| 129 | 743 | A743S | |
| 130 | 743 | A743P | |
| 131 | 744 | I744__K745insKIPVAI | |
| 132 | 745 | K745__L747del | |
| 133 | 745 | K745R | |
| 134 | 746 | E746del | |
| 135 | 746 | E746K | |
| 136 | 746 | E746V | |
| 137 | 751 | T751__I759 > S | |
| 138 | 751 | T751I | |
| 139 | 752 | S752_I759del | |
| 140 | 752 | S752Y | |
| 141 | 753 | P753P | |
| 142 | 753 | P753S | |
| 143 | 754 | K754R | |
| 144 | 755 | A755A | |
| 145 | 761 | D761__E762insEAFQ | |
| 146 | 764 | Y764Y | |
| 147 | 768 | S768-D770insIVD | |
| 148 | 768 | S768I + V769L | |
| 149 | 768 | S768I + V774M | |
| 150 | 769 | D769__D770 > GY | |

TABLE 1-continued

EGFR mutations

| No. | Position | Amino Acid | Type |
|-----|----------|------------|------|
| 151 | 769 | V769_D770insASV | |
| 152 | 769 | V769_D770insCV | |
| 153 | 769 | V769_D770insGSV | |
| 154 | 769 | V769_D770insGVV | |
| 155 | 769 | V769L | |
| 156 | 769 | V769M | |
| 157 | 769 | V769_D770insASV | |
| 158 | 769 | V769_D770insCV | |
| 159 | 769 | V769_D770insDNV | |
| 160 | 769 | V769_D770insGSV | |
| 161 | 769 | V769_D770insGVV | |
| 162 | 769 | V769-771 > VAS | |
| 163 | 770 | D770_N771insAPW | |
| 164 | 770 | D770_N771insG | |
| 165 | 770 | D770_N771insN | |
| 166 | 770 | D770_N771insSVD | |
| 167 | 770 | D770_N771insSVQ | |
| 168 | 770 | D770-P772 > DNV | |
| 169 | 770 | D770_N771 > AGG | |
| 170 | 770 | D770_N771insG | |
| 171 | 770 | D770_N771insN | |
| 172 | 770 | D770N | |
| 173 | 771 | N771-H773 > APW | |
| 174 | 771 | N771-H773insNPH | |
| 175 | 771 | N771_P772 > SVDNR | |
| 176 | 771 | N771 > GF | |
| 177 | 772 | P772_H773insX | |
| 178 | 772 | P772-H773insN | |
| 179 | 773 | H773_V774insH | |
| 180 | 773 | H773_V774insNPH | |
| 181 | 773 | H773_V774insPH | |
| 182 | 773 | H773_V774insH | |
| 183 | 773 | H773_V774insNPH | |
| 184 | 773 | H773_V774insPH | |
| 185 | 773 | H773 > NPY | |
| 186 | 773 | H773L | |
| 187 | 774 | V774_C775insHV | |
| 188 | 774 | V774M | |
| 189 | 774 | V774-776 > NPH | |
| 190 | 779 | G779F | |
| 191 | 783 | T783I | |
| 192 | 784 | S784F | |
| 193 | 787 | Q787R | |
| 194 | 792 | L792P | |
| 195 | 798 | L798F | |
| 196 | 803 | R803L | |
| 197 | 810 | G810S | |
| 198 | 810 | G810S | |
| 199 | 819 | V819V | |
| 200 | 833 | L833V | |
| 201 | 834 | V834L | |
| 202 | 841 | R841K | |
| 203 | 846 | K846R | |
| 204 | 847 | T847I | |
| 205 | 850 | H850N | |
| 206 | 851 | V851A | |
| 207 | 851 | V851I | |
| 208 | 853 | I853T | |
| 209 | 856 | F856L | |
| 210 | 864 | A864T | |
| 211 | 866 | E866K | |
| 212 | 872 | E872* | |
| 213 | 873 | G873E | |
| 214 | 897 | V897I | |
| 215 | 983 | G983_end | |
| 216 | 1036 | L1036_end | |
| 217 | 1038 | L1038 > [aa688-1038] | |
| 218 | 1048 | A1048V | |
| 219 | 1054 | G1054 > [aa688-1054] | |
| 220 | 1070 | S1070A | |
| 221 | 1071 | S1071A | |

In the table above mutations have been described as single events. It should be noted that in terms of frequency 90% of the sensitizing mutations are covered by exon 19 deletions (e.g positions 746 and 747, 61%) and exon 21 point mutations (L858R, 24%; L861Q, 4%). It should also be noted that complex mutation combination patterns are often observed (e.g. G719S+S768I). In acquired resistance where the resistance mutation (e.g. T790M) is acquired in an activating background, a complex combination pattern is a common rule.

In the first preferred embodiment of the present invention the mutation of the EGFR is an activating mutation, e.g selected from the group consisting of mutations identified in table 1 under No. 1 to 91, or, even more preferred, identified in table 1 under No. 1 to 29, 57 to 65, 73, 75, 76, 77, 79 and 80-91.

In the second preferred embodiment of the present invention the mutation of the EGFR is an activating mutation associated with a resistance or acquired resistance mutation to treatment with reversible EGFR and HER2 inhibitors such as gefitinib, erlotinib, vandetanib (ZD-6474), AEE-788, PKI-166, lapatinib, cetuximab, nimotuzumab, matuzumab, panitumumab, trastuzumab and pertuzumab or other irreversible inhibitors such as CI-1033, EKB-569, HKI-272 or HKI-357, e.g selected from the group consisting of mutations identified in table 1 under No. 92 to 97, or, even more preferred, identified in table 1 under No. 92, 93, 96, 96-a and 97.

According to a third subgroup of preferred embodiments of the present invention the mutation of the EGFR is predictive for Gefitinib and/or Erlotinib sensitivity and includes deletion of residues 747 (lysine) to 749 (glutamic acid) combined with a mutation in 750 (alanine), deletion of residues 747 (lysine) to 750 (alanine), substitution of arginine for leucine at residue 858, or substitution of glutamine for leucine at residue 861.

In a fourth preferred embodiment of the present invention the mutation of the EGFR is selected from the group consisting of T790M, E746_A750del, E746_S752>V, L747_P753>S, L858R, L747_A750>P, S752_I759del.

Examples of carcinomas showing resistance or acquired resistance to treatment with reversible EGFR and HER2 inhibitors such as gefitinib or erlotinib or to other irreversible inhibitors such as CI-1033, EKB-569, HKI-272 or HKI-357 within the scope of the invention include but are not limited to adenocarcinoma (AC), squamous cell carcinoma (SCC) and mixed or undifferentiated carcinomas. Carcinomas within the scope of the invention include but are not limited to the following histologies:

Head and neck tumours: SCC, AC, transitional cell cancers, mucoepidermoid cancers, undifferentiated carcinomas;

Central nervous system tumours: Astrocytoma, glioblastoma, meningeoma, neurinoma, schwannoma, ependymoma, hypophysoma, oligodendroglioma, medulloblastoma;

Bronchial and mediastinal tumours:
  Bronchial tumours:
    Small cell lung cancers (SCLC): oat-cell lung cancer, intermediate cell cancer, combined oat-cell lung cancer;
    Non-small cell lung cancers (NSCLC): SCC, spindle cell carcinoma, AC, bronchioalveolar carcinoma, large cell NSCLC, clear cell NSCLC;
  Mesothelioma;
  Thymoma;
  Thyroid carcinomas: papillary, follicular, anaplastic, medullary;
Tumours of the gastrointestinal tract:
  Oesophageal cancers: SCC, AC, anaplastic, carcinoid, sarcoma;

Gastric cancers: AC, adenosquamous, anaplastic;

Colorectal cancers: AC, including hereditary forms of AC, carcinoid, sarcoma;

Anal cancers: SCC, transitional epithelial cancer, AC, basal cell carcinoma;

Pancreatic cancers: AC, including ductal and acinary cancers, papillary, adenosquamous, undifferentiated, tumours of the endocrine pancreas;

Hepatocellular carcinoma, cholangiocarcinoma, angiosarcoma, hepatoblastoma;

Biliary carcinomas: AC, SCC, small cell, undifferentiated;

Gastrointestinal stroma tumours (GIST);

Gynaecological cancers:

Breast cancers: AC, including invasive ductal, lobular and medullary cancers, tubular, mucinous cancers, Paget-carcinoma, inflammatory carcinoma, ductal and lobular carcinoma in situ;

Ovarian cancers: Epithelial tumours, stroma tumours, germ cell tumours, undifferentiated tumours;

Cervical cancers: SCC, AC, mixed and undifferentiated tumours;

Endometrial cancers: AC, SCC, mixed, undifferentiated tumours;

Vulvar cancers: SCC, AC;

Vaginal cancers: SCC, AC;

Urinary tract and testicular cancers:

Testicular cancers: seminoma;

Non-seminomatous germ cell tumours: teratoma, embryonal cell carcinoma, choriocarcinoma, yolk sac tumour, mixed, Sertoli and Leydig-cell tumours;

Extragonadal germ cell tumours;

Prostate cancers: AC, small cell, SCC;

Renal cell cancers: AC, including clear cell, papillary and chromophobous carcinomas, hereditary forms (e.g. von-Hippel-Lindau syndrome), nephroblastoma;

Urinary bladder cancers: transitional cell (urothelial) cancers, SCC, AC;

Urethral cancers: SCC, transitional cell cancers, AC;

Penile cancers: SCC;

Tumours of endocrine tissue:

Thyroid cancers: papillary, follicular, anaplastic, medullary carcinomas, including MEN syndrome;

Tumours of the endocrine pancreas;

Carcinoids;

Pheochromocytoma.

Preferably, the resistant cancer indication is selected from the group consisting of Head and neck tumours: SCC, AC, transitional cell cancers, mucoepidermoid cancers, undifferentiated carcinomas;

Colorectal cancers, metastatic or non-metastatic: AC, including hereditary forms of AC, carcinoid, sarcoma;

Pancreatic cancers: AC, including ductal and acinary cancers, papillary, adenosquamous, undifferentiated, tumours of the endocrine pancreas;

Breast cancers, metastatic or non-metastatic: AC, including invasive ductal, lobular and medullary cancers, tubular, mucinous cancers, Paget-carcinoma, inflammatory carcinoma, ductal and lobular carcinoma in situ;

Prostate cancers: AC, small cell, SCC;

Non-small cell lung cancers (NSCLC): SCC, spindle cell carcinoma, AC, bronchioalveolar carcinoma, large cell NSCLC, clear cell NSCLC.

Within the meaning of the present invention, the following classes of chemotherapeutic agents (2) are especially of interest, although not representing a limitation:

Synthetic small molecule VEGF receptor antagonists

Small molecule growth factor (GF) receptor antagonists

Inhibitors of the EGF receptor and/or HER2 receptors and/or VEGF receptor and/or integrin receptors or any other protein tyrosine kinase receptors, which are not classified under the synthetic small-molecules Small molecule Polo-like kinase-1 (PLK-1) inhibitors Small molecule inhibitors of the Ras/Raf/MAPK or PI3K/AKT pathways or any other serine/threonine kinases.

Inhibitors of the Ras/Raf/MAPK or PI3K/AKT pathways or any other serine/threonine kinases, which are not classified under the synthetic small-molecules Inhibitors directed to EGF receptor and/or VEGF receptor and/or integrin receptors or any other protein tyrosine kinase receptors, which are synthetically manufactured antibodies, antibody fragments or fusion proteins Inhibitors directed to circulating VEGF, which are synthetically manufactured antibodies, antibody fragments or fusion proteins Inhibitors directed to the IGF1 receptor and/or IGF1 or IGF2 growth factor, which are synthetically manufactured chemical entities or antibodies, antibody fragments or fusion proteins Compounds which interact with nucleic acids and which are classified as alkylating agents or platinum compounds Compounds which interact with nucleic acids and which are classified as anthracyclines, as DNA intercalators or as DNA cross-linking agents Anti-metabolites Naturally occurring, semi-synthetic or synthetic bleomycin type antibiotics (BLM-group antibiotics)

Inhibitors of DNA transcribing enzymes, especially topoisomerase I or topoisomerase II inhibitors Chromatin modifying agents Mitosis inhibitors, anti-mitotic agents, or cell-cycle inhibitors Compounds interacting with or binding tubulin Compounds inhibiting mitotic kinesins or other motor proteins including but not limited to Eg5, CENP-E, MCAK, Kid, MKLP-1

Proteasome inhibitors

Heat shock protein inhibitors

Compounds targeting the anti-apoptotic function of Bcl-2, Bcl-$x_1$ and like molecules Enzymes Hormones, hormone antagonists or hormone inhibitors, or inhibitors of steroid biosynthesis Steroids Cytokines, hypoxia-selective cytotoxins, inhibitors of cytokines, lymphokines, antibodies directed against cytokines or oral and parenteral tolerance induction strategies Supportive agents Antiinflammatory compounds such as but not limited to COX-2 inhibitors Chemical radiation sensitizers and protectors Photochemically activated drugs Synthetic poly- or oligonucleotides Other chemotherapeutic or naturally occurring, semi-synthetic or synthetic therapeutic agents, such as cytotoxic antibiotics, antibodies targeting surface molecules of cancer cells, antibodies targeting growth factors or their receptors, inhibitors of metalloproteinases, inhibitors of oncogenes, inhibitors of gene transcription or of RNA translation or protein expression, or complexes of rare earth elements.

In another preferred embodiment of the invention the chemotherapeutic agent (2) is selected from the group consisting of a small molecule VEGF receptor antagonist such as vatalanib (PTK-787/ZK222584), SU-5416, SU-6668, SU-11248, SU-14813, AZD-6474, AZD-2171, CP-547632, CEP-7055, AG-013736, IM-842 or GW-786034, a dual EGFR/HER2 antagonist such as gefitinib, erlotinib, HKI-272, CI-1033 or GW-2016, an EGFR antagonist such as iressa (ZD-1839), tarceva (OSI-774), PKI-166, EKB-569 or herceptin, an antagonist of the mitogen-activated protein kinase such as BAY-43-9006 or BAY-57-9006, a protein kinase receptor antagonist which is not classified under the synthetic small molecules such as atrasentan, rituximab, cetuximab, Avastin™ (bevacizumab), bivatuzumab mertansine, IMC-1C11, erbitux (C-225), DC-101, EMD-72000, vitaxin, imatinib, a protein tyrosine kinase inhibitor which is a fusion protein such as VEGFtrap, an alkylating agent or a platinum compound such as melphalan, cyclophosphamide, an oxazaphosphorine, cisplatin, carboplatin, oxaliplatin, satraplatin, tetraplatin, iproplatin, mitomycin, streptozocin, carmustine (BCNU), lomustine (CCNU), busulfan, ifosfamide, streptozocin, thiotepa, chlorambucil, a nitrogen mustard such as mechlorethamine, an ethyleneimine compound, an alkylsulphonate, daunorubicin, doxorubicin (adriamycin), liposomal doxorubicin (doxil), epirubicin, idarubicin, mitoxantrone, amsacrine, dactinomycin, distamycin or a derivative thereof, netropsin, pibenzimol, mitomycin, CC-1065, a duocarmycin, mithramycin, chromomycin, olivomycin, a phtalanilide such as propamidine or stilbamidine, an anthramycin, an aziridine, a nitrosourea or a derivative thereof, a pyrimidine or purine analogue or antagonist or an inhibitor of the nucleoside diphosphate reductase such as cytarabine, 5-fluorouracile (5-FU), pemetrexed, tegafur/uracil, uracil mustard, fludarabine, gemcitabine, capecitabine, mercaptopurine, cladribine, thioguanine, methotrexate, pentostatin, hydroxyurea, or folic acid, a phleomycin, a bleomycin or a derivative or salt thereof, CHPP, BZPP, MTPP, BAPP, liblomycin, an acridine or a derivative thereof, a rifamycin, an actinomycin, adramycin, a camptothecin such as irinotecan (camptosar) or topotecan, an amsacrine or analogue thereof, a tricyclic carboxamide, an histonedeacetylase inhibitor such as SAHA, MD-275, trichostatin A, CBHA, LAQ824, or valproic acid, an anti-cancer drug from plants such as paclitaxel (taxol), docetaxel or taxotere, a vinca alkaloid such as navelbine, vinblastin, vincristin, vindesine or vinorelbine, a tropolone alkaloid such as colchicine or a derivative thereof, a macrolide such as maytansine, an ansamitocin or rhizoxin, an antimitotic peptide such as phomopsin or dolastatin, an epipodophyllotoxin or a derivative of podophyllotoxin such as etoposide or teniposide, a steganacin, an antimitotic carbamate derivative such as combretastatin or amphetinile, procarbazine, a proteasome inhibitor such as bortezomib, an enzyme such as asparaginase, pegylated asparaginase (pegaspargase) or a thymidine-phosphorylase inhibitor, a gestagen or an estrogen such as estramustine (T-66) or megestrol, an anti-androgen such as flutamide, casodex, anandron or cyproterone acetate, an aromatase inhibitor such as aminogluthetimide, anastrozole, formestan or letrozole, a GNrH analogue such as leuprorelin, buserelin, goserelin or triptorelin, an anti-estrogen such as tamoxifen or its citrate salt, droloxifene, trioxifene, raloxifene or zindoxifene, a derivative of 17β-estradiol such as ICI 164,384 or ICI 182,780, aminoglutethimide, formestane, fadrozole, finasteride, ketoconazole, a LH-RH antagonist such as leuprolide, a steroid such as prednisone, prednisolone, methylprednisolone, dexamethasone, budenoside, fluocortolone or triamcinolone, an interferon such as interferon β, an interleukin such as IL-10 or IL-12, an anti-TNFα antibody such as etanercept, TNF-α (tasonermin), an immunomodulatory drug such as thalidomide, its R- and S-enantiomers and its derivatives, or revimid (CC-5013), a leukotrien antagonist, mitomycin C, an aziridoquinone such as BMY-42355, AZQ or EO-9, a 2-nitroimidazole such as misonidazole, NLP-1 or NLA-1, a nitroacridine, a nitroquinoline, a nitropyrazoloacridine, a "dual-function" nitro aromatic such as RSU-1069 or RB-6145, CB-1954, a N-oxide of nitrogen mustard such as nitromin, a metal complex of a nitrogen mustard, an anti-CD3 or anti-CD25 antibody, a tolerance induction agent, a biphosphonate or derivative thereof such as minodronic acid or its derivatives (YM-529, Ono-5920, YH-529), zoledronic acid monohydrate, ibandronate sodium hydrate or clodronate disodium, a nitroimidazole such as metronidazole, misonidazole, benznidazole or nimorazole, a nitroaryl compound such as RSU-1069, a nitroxyl or N-oxide such as SR-4233, an halogenated pyrimidine analogue such as bromodeoxyuridine, iododeoxyuridine, a thiophosphate such as WR-2721, a photo-chemically activated drug such as porfimer, photofrin, a benzoporphyrin derivative, a pheophorbide derivative, merocyanin 540 (MC-540) or tin etioporpurin, an ant-template or an anti-sense RNA or DNA such as oblimersen, a non-steroidal inflammatory drug such as acetylsalicyclic acid, mesalazin, ibuprofen, naproxen, flurbiprofen, fenoprofen, fenbufen, ketoprofen, indoprofen, pirprofen, carprofen, oxaprozin, pranoprofen, miroprofen, tioxaprofen, suprofen, alminoprofen, tiaprofenic acid, fluprofen, indomethacin, sulindac, tolmetin, zomepirac, nabumetone, diclofenac, fenclofenac, alclofenac, bromfenac, ibufenac, aceclofenac, acemetacin, fentiazac, clidanac, etodolac, oxpinac, mefenamic acid, meclofenamic acid, flufenamic acid, nifluminic acid, tolfenamic acid, diflunisal, flufenisal, piroxicam, tenoxicam, lornoxicam, nimesulide, meloxicam, celecoxib, rofecoxib, or a pharmaceutically acceptable salt of a non-steroidal inflammatory drug, a cytotoxic antibiotic, an antibody targeting the surface molecules of cancer cells such as apolizumab or 1D09C3, an inhibitor of metalloproteinases such as TIMP-1 or TIMP-2, Zinc, an inhibitor of oncogenes such as P53 and Rb, a complex of rare earth elements such as the heterocyclic complexes of lanthanides, a photo-chemotherapeutic agent such as PUVA, an inhibitor of the transcription factor complex ESX/DRIP130/Sur-2, an inhibitor of HER-2 expression, such as the heat shock protein HSP90 modulator geldanamycin and its derivative 17-allylaminogeldanamycin or 17-AAG, or a therapeutic agent selected from IM-842, tetrathiomolybdate, squalamine, combrestatin A4, TNP-470, marimastat, neovastat, bicalutamide, abarelix, oregovomab, mitumomab, TLK-286, alemtuzumab, ibritumomab, temozolomide, denileukin diftitox, aldesleukin, dacarbazine, floxuridine, plicamycin, mitotane, pipobroman, plicamycin, tamoxifen and testolactone.

For instance, cancers may initially be diagnosed as gefitinib/erlotinib sensitive or predicted to be gefitinib/erlotinib sensitive by means of the methods described in Lynch et al., 2004; 350:2129-2139. Gefitinib/erlotinib sensitivity may be predicted by the presence in the tumor of EGFR mutations including, for example, deletion of residues 747 (lysine) to 749 (glutamic acid) combined with a mutation in 750 (alanine), deletion of residues 747 (lysine) to 750 (alanine), substitution of arginine for leucine at residue 858, of substitution of glutamine for leucine at residue 861.

Cancers may be diagnosed as resistant to treatment with reversible EGFR and HER2 inhibitors such as gefitinib or erlotinib or to treatment with other irreversible inhibitors such as CI-1033, EKB-569, HKI-272 or HKI-357 after treatment with the respective actives has commenced. Alternatively, cancers may be diagnosed as resistant to the actives mentioned hereinbefore prior to initiation of treatment with such compounds. For instance, Gefitinib and/or erlotinib resistance in the tumor may occur after, e.g., 6 months or longer of gefitinib and/or erlotinib treatment. Alternatively, gefitinib and/or erlotinib resistance of the tumor may be diagnosed less than 6 months after gefitinib and/or erlotinib treatment has commenced. Diagnosis of gefitinib and/or erlotinib resistance may be accomplished by way of monitoring tumor progression during gefitinib and/or erlotinib treatment. Tumor progression may be determined by comparison of tumor status between time points after treatment has commenced or by comparison of tumor status between a time point after treatment has commenced to a time point prior to initiation of gefitinib and/or erlotinib treatment. Tumor progression may be monitored during gefitinib and/or erlotinib treatment visually, for example, by means of radiography, for example, X-ray, CT scan, or other monitoring methods known to the skilled artisan, including palpitation of the cancer or methods to monitor tumor biomarker levels. Progression of the cancer during treatment with gefitinib and/or erlotinib indicates gefitinib and/or erlotinib resistance. A rise in level of tumor biomarkers indicates tumor progression. Thus, a rise in tumor biomarker levels during treatment with gefitinib and/or erlotinib indicates gefitinib and/or erlotinib resistance. Detection of new tumors or detection of metastasis indicates tumor progression. Cessation of tumor shrinkage indicates tumor progression. Growth of the cancer is indicated by, for example, increase in tumor size, metastasis or detection of new cancer, and/or a rise in tumor biomarker levels. The same applies analogously in the case of resistance to other actives mentioned hereinbefore.

The development of resistance to the actives mentioned hereinbefore may be monitored by means of testing for presence of a mutation associated with resistance to the respective active in circulating tumor cells obtained from the circulation, or other bodily fluid, of the subject. For instance, presence of gefitinib and/or erlotinib resistance associated mutations in tumor cells from the subject is indicative of a gefitinib and/or erlotinib resistant tumor.

In one embodiment, the subject's tumor harbors mutations indicative of gefitinib and/or erlotinib sensitivity, yet it is resistant to gefitinib and/or erlotinib treatment. In one embodiment, the subject's tumor harbors mutations indicative gefitinib and/or erlotinib sensitivity and harbors mutations indicative of gefitinib and/or erlotinib resistance, e.g., the T790M mutation, that is, where a methione residue is substituted for the native threonine residue, in EGFR, e.g. increased EGFR internalization. In one embodiment, the subject's tumor does not harbor mutations indicative of gefitinib and/or erlotinib sensitivity and does harbor mutations indicative of gefitinib and/or erlotinib resistance, e.g., the T790M mutation in EGFR, e.g., increased EGFR internalization.

In connection with the administration of the drug, an "effective amount" indicates an amount that results in a beneficial effect for at least a statistically significant fraction of patients, such as a improvement of symptoms, a cure, a reduction in disease load, reduction in tumor mass or cell numbers, extension of life, improvement in quality of life, or other effect generally recognized as positive by medical doctors familiar with treating the particular type of disease or condition.

Method of Treatment:

The method of treatment according to the invention comprises administration of therapeutically effective amount of BIBW 2992 (1) or a pharmaceutically acceptable salt thereof, preferably the dimaleate salt, optionally in combination with the administration of a further chemotherapeutic agent (2), to a patient in need thereof, [s.u.] optionally in combination with radiotherapy, radio-immunotherapy and/or tumour resection by surgery.

The term "therapeutically effective amount" shall mean that amount of a drug or pharmaceutical agent that will elicit the biological or medical response of a tissue, system, animal or human that is being sought by a researcher or clinician, resulting in a beneficial effect for at least a statistically significant fraction of patients, such as a improvement of symptoms, a cure, a reduction in disease load, reduction in tumor mass or cell numbers, extension of life, improvement in quality of life.

In accordance with the present invention BIBW 2992 (1) and the optional chemotherapeutic (2) may be administered by oral (including buccal or sublingual), enterical, parenteral (e.g., intramuscular, intraperitoneal, intravenous, transdermal or subcutaneous injection, or implant), nasal, vaginal, rectal, or topical (e.g. inhalative) routes of administration and may be formulated, alone or together, in suitable dosage unit formulations containing conventional non-toxic pharmaceutically acceptable carriers, adjuvants and vehicles appropriate for each route of administration.

In a preferred embodiment BIBW 2992 (1) is administered orally, enterically, transdermally, intravenously, peritoneally or by injection, preferably orally.

Dosages/BIBW 2992:

In one embodiment the invention relates to the method of treatment described above, characterised in that BIBW 2992 (1), or its polymorph, metabolite, hydrate, solvate, or a pharmaceutically acceptable salt thereof, is administered intermittent or in a daily dosage such that the plasma level of the active substance preferably lies between 10 and 5000 nM for at least 12 hours of the dosing interval.

BIBW 2992 (1) may be administered to the human patient in a daily dose of 0.01-4 mg/kg of body weight (bw), preferably 0.1-2 mg/kg, particularly preferred in a dose of 0.2-1.3 mg/kg bw. For oral treatment the compounds of formula (I) may be administered daily in a total dose of 10, 20, 30, 40, 50, 60, 70, 100, 200, or 300 mg, optionally divided into multiple doses, e.g. 1 to 3 doses to be administered through the day. Preferably the oral daily dose is administered only once a time. Especially for higher doses periods of treatment should alternate with periods of recovery, without administering the active of formula (I). For instance, treatment could follow a "7 day on—7 day off", a "14 day on—14 day off", a "21 day on 7 day off" or a continuous dosing schedule. "On-off" time periods can be chosen shorter, especially if higher doses are administered, or individually adapted to the needs of the patient.

The dosage for intravenous use of BIBW2992MA$_2$ may be 1-1000 mg, preferably 5-300 mg, particularly preferred 10-100 mg (dosages refer to the base form BIBW2992 (1)), either given as a bolus or, especially if higher doses are applied, as a slow intravenous infusion over several hours, e.g. over about 1, 2, 4, 6, 10, 12 or 24 hours.

However, it may optionally be necessary to deviate from the amounts specified, depending on the body weight or method of administration, the individual response to the medication, the nature of the formulation used and the time or interval over which it is administered. Thus, in some cases, it may be sufficient to use less than the minimum quantity specified above, while in other cases the upper limit specified will have to be exceeded. When large amounts are administered it may be advisable to spread them over the day in a number of single doses.

Dosages/Chemotherapeutic Agents (2):

Dosages and treatment schedules for the individual chemotherapeutic agents (2) are known in the art and may be applied analogously within the invention. Depending on the individual activity of the specific combination dosage of the chemotherapeutic agents (2) may be reduced, e.g. may vary in the range of 1/1 to 1/20 of the dosages described in the prior art.

For patients with metastatic breast cancer the combination with docetaxel may be given at a dose between 55 mg/m$^2$ and 100 mg/m$^2$ and most specifically at a dose of 60 to 75 mg/m$^2$ in administration schedule of once every 21 days. In a weekly administration schedule the dose of docetaxel may be lowered.

A similar dose range of docetaxel will be used in the treatment of hormone-refractory prostate cancer. In this case docetaxel is administered together with daily prednisone and/or with the administration of estramustine. The dose of estramustine is 14 mg per kg of body weight given in 3 or 4 divided doses daily. Most patients are treated at a dose range between 10 and 16 mg/kg body weight.

Docetaxel is also used in the treatment of non-small cell lung cancer at similar doses and schedules.

In patients with metastatic breast cancer, the administration of paclitaxel is at a dose of up to 175 mg/m$^2$ over 3 hours every 3 weeks. In a weekly administration schedule paclitaxel dose may be lower. In an adjuvant setting, paclitaxel will be administered at doses up to 175 mg/m$^2$ over 3 hours every 3 weeks sequentially to a combination with a doxorubicin-containing chemotherapy (four courses of doxorubicin and cyclophosphamide were used).

For patients with non-small cell lung cancer the recommended dose of paclitaxel is 135 mg/m$^2$ IV over 24 hours every 3 weeks. The administration of paclitaxel is followed by cisplatin at 75 mg/m$^2$. Another option is the combination of paclitaxel with carboplatin.

In patients with ovarian carcinoma, paclitaxel is used at a dose of 175 mg/m$^2$ IV over 3 hours followed by cisplatin at 75 mg/m$^2$ or at a dose of 135 mg/m$^2$ over 24 hours followed by cisplatin at a dose of 75 mg/m$^2$. Paclitaxel can also be combined with carboplatin. This cycle will be repeated every 3 weeks. Another treatment schedule in the more advanced disease setting is the administration of paclitaxel at either 135 or 175 mg/m$^2$ IV over 3 hours every 3 weeks.

Carboplatin is administered as a single agent in recurrent ovarian carcinoma at a dose of 360 mg/m$^2$ IV on day 1 every 4 weeks. In advanced ovarian carcinoma it is used at a dose of 300 mg/m$^2$ on day 1 every 4 weeks for six cycles together with cyclophosphomide 600 mg/m$^2$ on day 1 every four weeks for 6 cycles. Carboplatin is also used in combination with paclitaxel for the treatment of advanced ovarian cancer and advanced non-small cell lung cancer.

In patients with breast cancer and colorectal cancer, the administration of capecitabine is used at a dose of up to 1250 mg/m$^2$ twice daily for 2 weeks followed by a 1-week rest before repating this 3-week regimen. Such a dose will also be used in the adjuvant treatment of colorectal cancer for a total of eight 3-week cycles. When combining with drugs like docetaxel dose reductions according to actually experienced side effects may become necessary.

In patients with metastatic breast cancer, gemcitabine at a dose of 1250 mg/m$^2$ over 30 minutes on days 1 and 8 of each 21-day treatment cycle will be used in combination with paclitaxel. Paclitaxel should be administered at 175 mg/m$^2$ as a 3-hour infusion before the administration of gemcitabine on day 1.

Gemcitabine is also used for the treatment of pancreatic cancer at a dose of up to 1000 mg/m$^2$ over 30 minutes once weekly for up to 7 weeks (or until toxicity necessitates reducing or holding the dose) followed by a week of rest. Subsequent cycles will be administration for 3 consecutive weeks every 4 weeks.

In non-small cell lung cancer, gemcitabine is used in two schedules. In the first schedule, gemcitabine is administered at 1000 mg/m$^2$ over 30 minutes on days 1, 8, and 15 every 4 weeks. Cisplatin is administerd at 100 mg/m$^2$ IV on day 1 after the infusion of gemcitabine. In another schedule gemcitabine is administered at 1250 mg/m$^2$ IV over 30 minutes on days 1 and 8 every 3 weeks. Cisplatin should be administered at 100 mg/m$^2$ IV on day 1.

Trastuzumab is used either single agent or in combination with paclitaxel for the treatment of HER2-positive breast cancer. Trastuzumab is recommended at an initial loading dose of of 4 mg/kg as a 90-minute infusion. The weekly recommended maintenance dose is 2 mg/kg as a 30 minute infusion. Additional dose schedules are under consideration.

In combination with a dosing schedule (FOLFOX4) for the treatment of colorectal cancer, oxaliplatin may be administerd on day 1 in a dose of up to 85 mg/m$^2$ (in infusions of up to 2 hours or more). Leucovorin in this schedule may be up to 200 mg/m$^2$ (in infusions of up to 2 hours or more) while fluorouracil may used in doses up to 400 mg/m$^2$ (bolus) followed by infusion of 600 mg/m$^2$ over 22 hours. On day 2, the administration will be leucovorin may be up to 200 mg/m$^2$ (in infusions of up to 2 hours or more) while fluorouracil may used in doses up to 400 mg/m$^2$ (bolus) followed by infusion of 600 mg/m$^2$ over 22 hours. Such an regimen may be repeated every 2 weeks. Other treatment schedules based on variations of administration lengths of oxaliplatin, leucovorin and fluorouracil may also apply.

Also in the treatment of colorectal cancer other schedules may be used. These include irinotecan 125 mg/m$^2$ as a 90 minute infusion, leucovorin as a 20 mg/m$^2$ (15 minute bolus or IV push) followed by fluorouracil 500 mg/m$^2$ (bolus every week×4). This schedule will be repeated every 6 weeks. Another treatment schedule is the administration of irinotecan 180 mg/m$^2$ as a 90 minute infusion (day 1, 15, 29), leucovorin at 200 mg/m$^2$ over 2 hours (days 1, 2, 15, 16, 29, 30), and fluorouracil as 400 mg/m$^2$ bolus followed by an infusion of 600 mg/m$^2$ over 22 hours (both on days 1, 2, 15, 16, 29, 30). This schedule will be repeated on day 43. Other treatment schedules based on variations of administration lengths of irinotecan, leucovorin and fluorouracil may also apply.

Irinotecan may also applied for colorectal cancer in a dosing schedule of 125 mg/m$^2$ over 90 minutes on days 1, 8, 15, 22 followed by 2 week rest before repeating the schedule. Another option would be dosing of irinotecan at 350 mg/m$^2$ over 90 minutes every 3 weeks.

Another treatment schedule for colorectal cancer may be administered by combination with leucovorin at 200 mg/m$^2$ (2-hour infusion) followed by fluorouracil 400 mg/m$^2$ (bolus) and 600 mg/m$^2$ (22 hour infusion) at day 1. On day 2 this schedule is repeated. Such a schedule is repeated every 2 weeks. Other treatment schedules based on variations of administration lengths of leucovorin and fluorouracil may also apply.

However, it may optionally be necessary to deviate from the amounts specified, depending on the body weight or method of administration, the individual response to the medication, the nature of the formulation used and the time or interval over which it is administered. Thus, in some cases, it may be sufficient to use less than the minimum quantity specified above, while in other cases the upper limit specified will have to be exceeded. When large amounts are administered it may be advisable to spread them over the day in a number of single doses.

Dosages/Radiotherapy or Radio-Immunotherapy:

Dosages and treatment schedules for radiotherapy and radio-immunotherapy are known in the art and may be applied analogously within the invention. Depending on the individual activity of the specific combination with BIBW 2992 (1) and, optionally, chemotherapeutic agent (2), dosage of the radiotherapy and radio-immunotherapy component may be reduced, e.g. may vary in the range of 1/1 to 1/20 of the dosages described in the prior art.

Pharmaceutical Compositions:

As used herein, the term "composition" is intended to encompass a product comprising the specified ingredients in the specified amounts, as well as any product which results, directly or indirectly, from a combination of the specified ingredients in the specified amounts. The amount of pharmaceutically active compound in each case should be in the range from 0.1-90 wt. %, preferably 0.5-50 wt. % of the total composition, i.e. in amounts which are sufficient to achieve the dosage ranges given hereinbefore. The doses specified may, if necessary, be given several times a day.

As already mentioned before, within the meaning of the present invention, the components BIBW 2992 (1) and optional component (2) may be administered separately (which implies that they are formulated separately) or together (which implies that they are formulated together). Hence, the administration of one element of the combination of the present invention may be prior to, concurrent to, or subsequent to the administration of the other element of the combination.

The pharmaceutical compositions for the administration of the components BIBW 2992 (1) and (2) of this invention may conveniently be presented in dosage unit form and may be prepared by any of the methods well known in the art of pharmacy. All methods include the step of bringing the active ingredient into association with the carrier which is constituted of one or more accessory ingredients. In general, the pharmaceutical compositions are prepared by uniformly and intimately bringing the active ingredients into association with a liquid carrier or a finely divided solid carrier or both, and then, if necessary, shaping the product into the desired dosage form. In the pharmaceutical compositions the active compounds are included in an amount sufficient to produce the desired pharmacologic effect.

Suitable excipients may be, for example, water, pharmaceutically acceptable organic solvents, such as paraffins (e.g. petroleum fractions), oils of vegetable origin (e.g. groundnut or sesame oil), mono- or polyfunctional alcohols (e.g. ethanol or glycerol), carriers such as e.g. natural mineral powders (e.g. kaolin, clays, talc, chalk), synthetic mineral powders (e.g. highly dispersed silica and silicates), sugar (e.g. glucose, lactose and dextrose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

The preparations are administered in the usual way, preferably by oral or transdermal route, particularly preferably by oral route. When administered orally the tablets may, of course, contain additives, such as e.g. sodium citrate, calcium carbonate and dicalcium phosphate together with various additives, such as starch, preferably potato starch, gelatine and the like, in addition to the abovementioned carriers. Lubricants such as magnesium stearate, sodium laurylsulphate and talc may also be used to form tablets. In the case of aqueous suspensions the active substances may be combined with various flavour enhancers or colourings in addition to the abovementioned excipients.

For parenteral use, solutions of the active substances may be prepared using suitable liquid carrier materials.

The pharmaceutical compositions containing the active ingredients BIBW 2992 (1) and (2), separately or together, that are suitable for oral administration may be in the form of discrete units such as hard or soft capsules, tablets, troches or lozenges, each containing a predetermined amount of the active ingredients, or in the form of a dispersible powder or granules, or in the form of a solution or a suspension in an aqueous liquid or non-aqueous liquid, or in the form of syrups or elixirs, or in the form of an oil-in-water emulsion or a water-in-oil emulsion.

Dosage forms intended for oral use may be prepared according to any method known to the art for the manufacture of pharmaceutical formulations and such compositions. The excipients used may be, for example: (a) inert diluents such as mannitol, sorbitol, calcium carbonate, pregelatinized starch, lactose, calcium phosphate or sodium phosphate; (b) granulating and disintegrating agents, such as povidone, copovidone, hydroxypropylmethylcellulose, corn starch, alginic acid, crospovidone, sodiumstarchglycolate, croscarmellose, or polacrilin potassium; (c) binding agents such as microcrystalline cellulose or acacia; and (d) lubricating agents such as magnesium stearate, stearic acid, fumaric acid or talc.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Capsules containing one or more active substances or combinations of active substances may for example be prepared by mixing the active substances with inert carriers such as lactose or sorbitol and packing them into gelatine capsules. In some cases, formulations for oral use may be in the form of hard gelatin or HPMC (hydroxypropylmethylcellulose) capsules wherein the active ingredients BIBW 2992 (1) or (2), separately or together, is mixed with an inert solid diluent, for example pregelatinized starch, calcium carbonate, calcium phosphate or kaolin, or dispensed via a pellet formulation. They may also be in the form of soft gelatin capsules wherein the active ingredient is mixed with water or an oil medium, for example peanut oil, liquid paraffin, medium chain triglycerides or olive oil.

The tablets, capsules or pellets may be uncoated or they may be coated by known techniques to delay disintegration and absorption in the gastrointestinal tract and thereby provide a delayed action or sustained action over a longer period. For example, a time delay material such as celluloseacetate phtalate or hydroxypropylcellulose acetate succinate or sustained release material such as ethylcellulose or ammoniomethacrylate copolymer (type B) may be employed.

Liquid dosage forms for oral administration in accordance with the present invention include pharmaceutically acceptable emulsions, solutions, suspensions, syrups, and elixirs containing inert diluents commonly used in the art, such as water. Besides such inert diluents, compositions can also include adjuvants, such as wetting agents, emulsifying and suspending agents, and sweetening, flavoring, perfuming and preserving agents.

Syrups or elixirs containing the active substances or combinations thereof according to the invention may additionally contain a sweetener such as saccharin, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Definitions:

The terms "ErbB 1", "epidermal growth factor receptor" and "EGFR" are used interchangeably herein and refer to native sequence EGFR as disclosed, for example, in Carpenter et al. Ann. Rev. Biochem. 56:881-914 (1987), including variants thereof (e.g. a deletion mutant EGFR as in Humphrey et al. PNAS (USA) 87:4207-4211 (1990)). erbB1 refers to the gene encoding the EGFR protein product. As used herein, the EGFR protein is disclosed as GenBank accession no. NP_005219 which is encoded by the erbB1 gene, GenBank accession no. NM_005228. The sequences are disclosed as SEQ ID NO: 1, and SEQ ID NO: 2, respectively, in FIG. 5 of WO 2006/084058.

The term "activating mutation of the EGFR" as used herein refers to a variance (i.e. mutation) in the nucleotide sequence of erbB1, the gene gene encoding the EGFR, that results in an increased kinase activity. The increased kinase activity is a direct result of the variance in the nucleic acid and is associated with the protein for which the gene encodes.

The following Examples serve to illustrate the invention without restricting it:

Example 1

Coated Tablets Containing 75 mg of Active Substance

| 1 tablet core contains: | |
| --- | --- |
| active substance | 75.0 mg |
| calcium phosphate | 93.0 mg |
| corn starch | 35.5 mg |
| polyvinylpyrrolidone | 10.0 mg |
| hydroxypropylmethylcellulose | 15.0 mg |
| magnesium stearate | 1.5 mg |
| | 230.0 mg |

Preparation:

The active substance is mixed with calcium phosphate, corn starch, polyvinylpyrrolidone, hydroxypropylmethylcellulose and half the specified amount of magnesium stearate. Blanks 13 mm in diameter are produced in a tablet-making machine and these are then rubbed through a screen with a mesh size of 1.5 mm using a suitable machine and mixed with the rest of the magnesium stearate. This granulate is compressed in a tablet-making machine to form tablets of the desired shape.

| Weight of core: | 230 mg |
| --- | --- |
| die: | 9 mm, convex |

The tablet cores thus produced are coated with a film consisting essentially of hydroxypropylmethylcellulose. The finished film-coated tablets are polished with beeswax.

| Weight of coated tablet: | 245 mg. |
| --- | --- |

Example 2

Tablets Containing 100 mg of Active Substance

| 1 tablet contains: | |
| --- | --- |
| active substance | 100.0 mg |
| lactose | 80.0 mg |
| corn starch | 34.0 mg |
| polyvinylpyrrolidone | 4.0 mg |
| magnesium stearate | 2.0 mg |
| | 220.0 mg |

Preparation:

The active substance, lactose and starch are mixed together and uniformly moistened with an aqueous solution of the polyvinylpyrrolidone. After the moist composition has been screened (2.0 mm mesh size) and dried in a rack-type drier at 50° C. it is screened again (1.5 mm mesh size) and the lubricant is added. The finished mixture is compressed to form tablets.

| Weight of tablet: | 220 mg |
| --- | --- |
| Diameter: | 10 mm, biplanar, facetted on both sides and notched on one side. |

Example 3

Tablets Containing 150 mg of Active Substance

1 Tablet Contains:

| | |
| --- | --- |
| active substance | 150.0 mg |
| powdered lactose | 89.0 mg |
| corn starch | 40.0 mg |
| colloidal silica | 10.0 mg |
| polyvinylpyrrolidone | 10.0 mg |
| magnesium stearate | 1.0 mg |
| | 300.0 mg |

Preparation:

The active substance mixed with lactose, corn starch and silica is moistened with a 20% aqueous polyvinylpyrrolidone solution and passed through a screen with a mesh size of 1.5 mm. The granules, dried at 45° C., are passed through the same screen again and mixed with the specified amount of magnesium stearate. Tablets are pressed from the mixture.

| Weight of tablet: | 300 mg |
| --- | --- |
| die: | 10 mm, flat |

Example 4

Hard Gelatine Capsules Containing 150 mg of Active Substance

| 1 capsule contains: | |
|---|---|
| active substance | 50.0 mg |
| corn starch (dried) | approx. 80.0 mg |
| lactose (powdered) | approx. 87.0 mg |
| magnesium stearate | 10.0 mg |
| | approx. 420.0 mg |

Preparation:

The active substance is mixed with the excipients, passed through a screen with a mesh size of 0.75 mm and homogeneously mixed using a suitable apparatus. The finished mixture is packed into size 1 hard gelatine capsules.

| Capsule filling: | approx. 320 mg |
|---|---|
| Capsule shell: | size 1 hard gelatine capsule. |

Example 5

Suppositories Containing 150 mg of Active Substance

1 Suppository Contains:

| | |
|---|---|
| active substance | 150.0 mg |
| polyethyleneglycol 1500 | 550.0 mg |
| polyethyleneglycol 6000 | 460.0 mg |
| polyoxyethylene sorbitan monostearate | 840.0 mg |
| | 2,000.0 mg |

Preparation:

After the suppository mass has been melted the active substance is homogeneously distributed therein and the melt is poured into chilled moulds.

Example 6

Suspension Containing 50 mg of Active Substance

| 100 ml of suspension contain: | |
|---|---|
| active substance | 1.00 g |
| carboxymethylcellulose-Na-salt | 0.10 g |
| methyl p-hydroxybenzoate | 0.05 g |
| propyl p-hydroxybenzoate | 0.01 g |
| glucose | 10.00 g |
| glycerol | 5.00 g |
| 70% sorbitol solution | 20.00 g |
| flavouring | 0.30 g |
| dist. water ad | 100.0 ml |

Preparation:

The distilled water is heated to 70° C. The methyl and propyl p-hydroxybenzoates together with the glycerol and sodium salt of carboxymethylcellulose are dissolved therein with stirring. The solution is cooled to ambient temperature and the active substance is added and homogeneously dispersed therein with stirring. After the sugar, the sorbitol solution and the flavouring have been added and dissolved, the suspension is evacuated with stirring to eliminate air.

5 ml of suspension contain 50 mg of active substance.

Example 7

Ampoules Containing 10 mg Active Substance

| Composition: | |
|---|---|
| active substance | 10.0 mg |
| 0.01 N hydrochloric acid q.s. | |
| double-distilled water ad | 2.0 ml |

Preparation:

The active substance is dissolved in the requisite amount of 0.01 N HCl, made isotonic with common salt, filtered sterile and transferred into 2 ml ampoules.

Example 8

Ampoules Containing 50 mg of Active Substance

| Composition: | |
|---|---|
| active substance | 50.0 mg |
| 0.01 N hydrochloric acid q.s. | |
| double-distilled water ad | 10.0 ml |

Preparation:

The active substance is dissolved in the necessary amount of 0.01 N HCl, made isotonic with common salt, filtered sterile and transferred into 10 ml ampoules.

Example 9

Capsules for Powder Inhalation Containing 5 mg of Active Substance

| 1 capsule contains: | |
|---|---|
| active substance | 5.0 mg |
| lactose for inhalation | 15.0 mg |
| | 20.0 mg |

Preparation:

The active substance is mixed with lactose for inhalation. The mixture is packed into capsules in a capsule-making machine (weight of the empty capsule approx. 50 mg).

| weight of capsule: | 70.0 mg |
|---|---|
| size of capsule | 3 |

Example 10

Solution for Inhalation for Hand-Held Nebulisers Containing 2.5 mg Active Substance

| 1 spray contains: | |
|---|---|
| active substance | 2.500 mg |
| benzalkonium chloride | 0.001 mg |
| 1N hydrochloric acid q.s. | 2.500 mg |
| ethanol/water (50/50) ad | 15.000 mg |

Preparation:

The active substance and benzalkonium chloride are dissolved in ethanol/water (50/50). The pH of the solution is adjusted with 1N hydrochloric acid. The resulting solution is filtered and transferred into suitable containers for use in hand-held nebulisers (cartridges).

Contents of the container: 4.5 g

The invention claimed is:

1. A method of treating patients suffering from cancer selected from the group consisting of
    Central nervous system tumours selected from the group consisting of:
    Astrocytoma, glioblastoma, meningeoma, neurinoma, schwannoma, ependymoma, hypophysoma, oligodendroglioma and medulloblastoma;
    Ovarian cancers selected from the group consisting of:
    Epithelial tumours, stroma tumours, germ cell tumours and undifferentiated tumours;
    Prostate cancers selected from the group consisting of: AC, small cell and SCC;
    said cancers harbouring a mutation of the EGFR gene in the tumour, wherein the EGFR mutation is an activating mutation selected from the group of mutations identified in table 1 under No. 1 to 29, 57 to 65, 73, 75, 76, 77, 79 and 80-91,
    wherein the cancer shows resistance or acquired resistance to treatment with reversible EGFR and HER2 inhibitors or to other irreversible inhibitors selected from CI-1033, EKB-569, HKI-272 or HKI-357,
    said method consisting of administering a therapeutically effective amount of the single irreversible EGFR inhibitor BIBW 2992 (1) to a patient in need thereof, optionally in combination with radiotherapy, radio-immunotherapy and/or tumour resection by surgery.

2. The method of claim 1, wherein the cancer shows resistance or acquired resistance to treatment with gefitinib and/or erlotinib.

3. The method of claim 1, wherein the EGFR mutation is selected from the group of mutations identified in table 1 under No. 92 to 97.

4. The method of claim 1, wherein the EGFR mutation is selected from the group of mutations identified in table 1 under No. 92, 93, 96, 96-a and 97.

5. The method of claim 1, wherein the EGFR mutation is selected from the group consisting of T790M, E746_A750del, E746_S752>V, L747_P753>S, L858R, L747_A750>P, S752__1759del.

* * * * *